(12) United States Patent
Hu et al.

(10) Patent No.: US 9,646,370 B2
(45) Date of Patent: May 9, 2017

(54) AUTOMATIC DETECTION METHOD FOR DEFECTS OF A DISPLAY PANEL

(71) Applicant: Shenzhen China Star Optoelectronics Technology Co., Ltd., Shenzhen, Guangdong (CN)

(72) Inventors: Houliang Hu, Guangdong (CN); Li-wei Chu, Guangdong (CN)

(73) Assignee: Shenzhen China Star Optoelectronics Technology Co., Ltd, Shenzhen, Guangdong (CN)

(*) Notice: Subject to any disclaimer, the term of this patent is extended or adjusted under 35 U.S.C. 154(b) by 171 days.

(21) Appl. No.: 14/425,048

(22) PCT Filed: Jan. 20, 2015

(86) PCT No.: PCT/CN2015/071129
§ 371 (c)(1),
(2) Date: Mar. 1, 2015

(87) PCT Pub. No.: WO2016/095318
PCT Pub. Date: Jun. 23, 2016

(65) Prior Publication Data
US 2016/0343121 A1 Nov. 24, 2016

(30) Foreign Application Priority Data
Dec. 16, 2014 (CN) .......................... 2014 1 0782236

(51) Int. Cl.
*G06K 9/40* (2006.01)
*G06T 7/00* (2017.01)
(Continued)

(52) U.S. Cl.
CPC ........... *G06T 7/0004* (2013.01); *G01N 21/88* (2013.01); *G01N 21/8851* (2013.01);
(Continued)

(58) Field of Classification Search
None
See application file for complete search history.

(56) References Cited

U.S. PATENT DOCUMENTS

| 5,717,780 A * | 2/1998 | Mitsumune | ............. G06T 7/001 348/92 |
| 5,754,678 A * | 5/1998 | Hawthorne | ........... G06T 7/0004 324/760.01 |

(Continued)

FOREIGN PATENT DOCUMENTS

| CN | 102202226 | * | 9/2011 | |
| CN | 102202226 A | | 9/2011 | |
| CN | 202253135 | * | 5/2012 | ........... G02B 6/0088 |
| CN | 202253135 U | | 5/2012 | |

OTHER PUBLICATIONS

Chinese Master's Theses.
Polymer Light-emitting Diode Defect Inspecting System.

*Primary Examiner* — Randolph I Chu
(74) *Attorney, Agent, or Firm* — Andrew C. Cheng

(57) ABSTRACT

An automatic detection method for defects of a display panel is disclosed, which comprises: acquiring a tag image, a mapped original image and a mapped tag image; dividing the mapped original image into a plurality of mapped original sub-images, and dividing the mapped tag image into a plurality of mapped tag sub-images; acquiring a normal area and a defective area of the mapped original sub-images; merging the mapped original sub-images to discriminate the normal area and the defective area of the mapped original sub-images; correcting the discriminated normal area and the discriminated defective area of the mapped original sub-images by using the mapped tag image and the tag image to acquire a defect location of the display panel. The automatic detection method for defects of the display panel can accurately acquire the location of the defect and the (Continued)

difference between the defective area and the normal area to quantify and discriminate the defects of the display panel.

13 Claims, 1 Drawing Sheet

(51) Int. Cl.
    *G01N 21/88*      (2006.01)
    *G02F 1/13*      (2006.01)

(52) U.S. Cl.
    CPC ........ *G06T 7/001* (2013.01); *G01N 2021/889* (2013.01); *G02F 1/13* (2013.01); *G06T 2207/30121* (2013.01)

(56) References Cited

U.S. PATENT DOCUMENTS

| | | | | |
|---|---|---|---|---|
| 5,790,694 A * | 8/1998 | Maruo | ................ | G06T 7/0008 382/149 |
| 5,917,957 A * | 6/1999 | Ichikawa | ................ | G06T 7/001 382/274 |
| 6,122,397 A * | 9/2000 | Lee | ................ | G06T 7/001 382/141 |
| 2008/0107328 A1* | 5/2008 | Chen | ................ | G06T 7/0004 382/149 |
| 2009/0238446 A1* | 9/2009 | Kataoka | ................ | G03F 1/84 382/152 |
| 2014/0270347 A1* | 9/2014 | Xu | ................ | G06K 9/6282 382/103 |
| 2014/0355873 A1* | 12/2014 | Sah | ................ | G06T 7/0004 382/165 |

\* cited by examiner

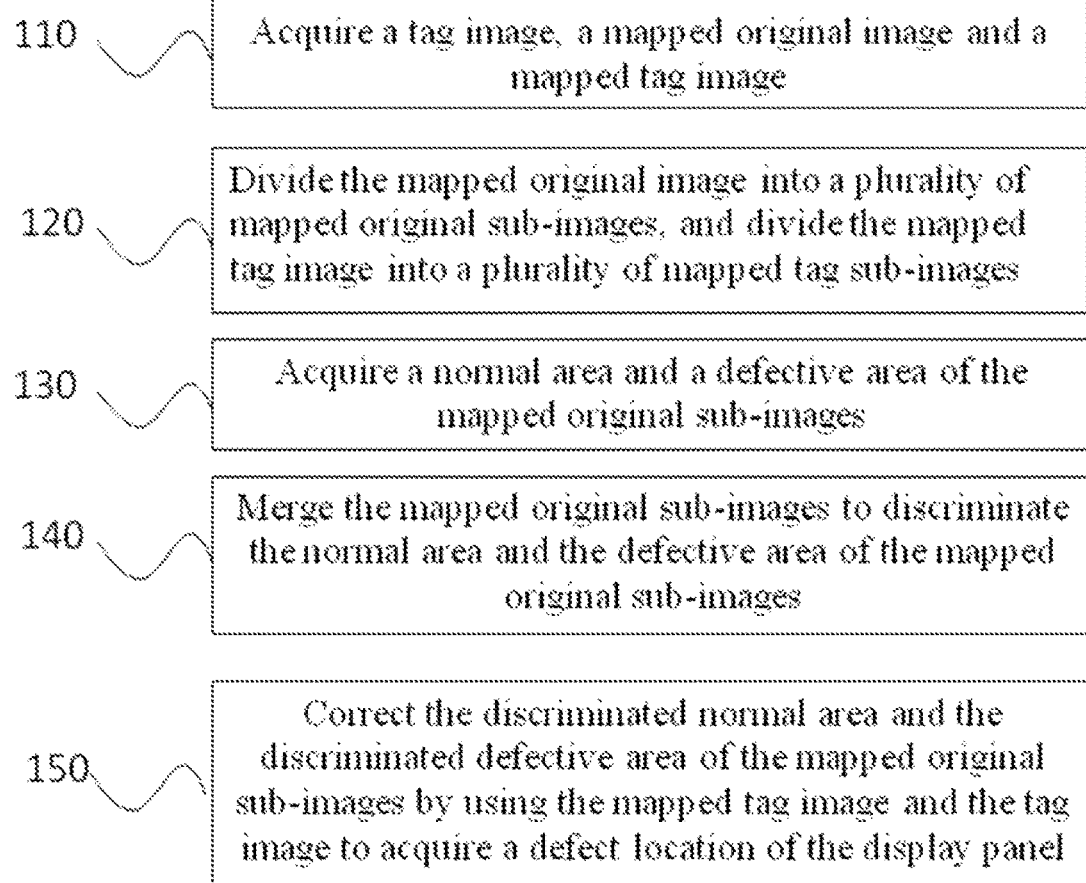

AUTOMATIC DETECTION METHOD FOR DEFECTS OF A DISPLAY PANEL

FIELD OF THE INVENTION

The present invention relates to a manufacturing technical field of a display panel; in particular, to an automatic detection method for defects of the display panel during the manufacturing process of the display panel.

BACKGROUND OF THE INVENTION

The display panel having high quality images can be achieved with the rapid development of the display technologies (such as LCD panel or OLED panel). They have already become the mainstream of the market. However, in light of the conventional manufacturing technology for the display panel, it is very difficult to avoid the display defect. Therefore, it is very necessary to inspect the panel defects of the display panel during the manufacturing process.

In the convention method for examining the defects of the display panel, an original image of the display panel is acquired from a camera, and then the original image is transferred to the computer which analyzes the original image to acquire the defects of the display panel. However, the conventional method cannot accurately get the defect location and the difference between the defect area and the normal area so that the defects of the display panel cannot be quantified and discriminated.

SUMMARY OF THE INVENTION

In light of the problems existing in the conventional art, the present invention provides an automatic detection method for defects of a display panel, comprises: acquiring a tag image, a mapped original image and a mapped tag image; dividing the mapped original image into a plurality of mapped original sub-images, and dividing the mapped tag image into a plurality of mapped tag sub-images; acquiring a normal area and a defective area of the mapped original sub-images; merging the mapped original sub-images to discriminate the normal area and the defective area of the mapped original sub-images; correcting the discriminated normal area and the discriminated defective area of the mapped original sub-images by using the mapped tag image and the tag image to acquire a defect location of the display panel.

Further, the step of acquiring a tag image, a mapping original image and a mapping tag image comprises: marking a plurality of tag points in the original image displayed on the display panel to acquire the tag image; sampling the original image and the tag image to acquire a sampled original image and a sampled tag image; respectively cutting the original sampled image and the tag sampled image by using a plurality of corner points, to acquire a cut original image and a cut tag image; respectively rotating the cut original image and the cut tag image to acquire a rotated original image and a rotated tag image; respectively cutting again and stretching the rotated original image and the rotated tag image to acquire a stretched original image and a stretched tag image; respectively black-pixel-inserting the stretched original image and the stretched tag image, and filling a black pixel by using a linear interpolation method to acquire the mapped original image and the mapped tag image.

Further, resolution of the mapped original image is same as resolution of the original image, and resolution of the mapped tag image is same as resolution of the original image.

Further, a method of determining the corner points comprises: setting up a plurality of mask matrixes, wherein amount of the mask matrixes is same as amount of the tag points; convolution calculating the sampled tag image by using the mask matrixes to get a convolution value; determining if Euclidean distance between a point with the convolution value larger than a predetermined threshold value and a top point of the sampled tag image is shortest; defining the point with the convolution value larger than the predetermined threshold value and having the shortest Euclidean distance to the top point of the sampled tag image as the corner point.

Further, the step of acquiring the normal area and the defective area of the mapped original sub-image further comprises: acquiring a luminance histogram of the mapped original sub-image; determining the maximum luminance value and the minimum luminance value based on the luminance histogram; determining if a luminance value of a pixel in the mapping original sub-image is larger than the minimum luminance value and smaller than the maximum luminance value; if the luminance value of the pixel in the mapping original sub-image is larger than the minimum luminance value and smaller than the maximum luminance value, the pixel of the mapped original sub-image is the normal area.

Further, if the luminance value of the pixel in the mapped original sub-image is not larger than the minimum luminance value or smaller than the maximum luminance value, the pixel of the mapped original sub-image is the defective area.

Further, a method of determining the maximum luminance value and the minimum luminance value comprises: in the luminance histogram, a determining amount ratio of the maximum luminance value and the minimum luminance value is not smaller than a predetermining amount ratio of a maximum luminance initial value and a minimum luminance initial value; computing a first weighted average value larger than the luminance value of the pixel in the mapped original sub-image of the maximum luminance initial value, and computing a second weighted average value smaller than the luminance value of the pixel in the mapped original sub-image of the minimum luminance initial value; when a different value between the first weighted average value and the maximum luminance initial value is larger than a threshold value, and a different value between the minimum luminance initial value and the second weighted average value is larger than the threshold value, the maximum luminance initial value and the minimum luminance initial value are respectively defined as the maximum luminance value and the minimum luminance value.

Further, when the difference value between the first weighted average value and the maximum luminance initial value is not larger than the threshold value and/or the difference value between the second weighted average value and the minimum luminance initial value is not larger than the threshold value, the predetermined amount ratio pluses 0.01 and the maximum luminance initial value and the minimum luminance initial value are redefined.

Further, a method of determining the maximum luminance value and the minimum luminance value comprises: when the predetermined amount ratio is 1, the maximum luminance initial value and the minimum luminance initial value are defined as the maximum luminance value and the minimum luminance value.

Further, the step of correcting the discriminated normal area and the discriminated defective area of the mapped original sub-images comprises: computing a plurality of tag points in the stretched tag image and a plurality of corresponding coordinate deviation values of the tag points of the tag image; correcting the discriminated normal area and the discriminated defective area of the mapped original image by using the corresponding coordinate deviation values.

The automatic detection method for defects of a display panel of the embodiments of the present invention accurately acquires the location of the defect and the difference between the defective area and the normal area to quantify and discriminate the defects of the display panel.

BRIEF DESCRIPTION OF THE DRAWINGS

The following description in conjunction with the accompanying drawings, the above and other aspects, features and advantages of embodiments of the present invention will become apparent from the drawings in which:

FIG. 1 is a flow chart of an automatic detection method for defects of a display panel based on the embodiment of the present invention.

DETAILED DESCRIPTION OF THE PREFERRED EMBODIMENTS

Hereinafter, embodiments of the present invention will be described in detail with reference to the accompanying drawings. However, be in many different forms and embodiments of the present invention, and the present invention should not be construed as limited to the specific embodiments set forth herein. Rather, these embodiments are provided to explain the principles of the invention and its practical application so that others skilled in the art to understand the invention for various embodiments and various modifications suited to the particular intended application FIG. 1 is a flow chart of an automatic detection method for defects of a display panel based on the embodiment of the present invention.

Refer to FIG. 1. The step S110 is to acquire a tag image, a mapped original image and a mapped tag image.

Here, the step of acquiring a tag image, a mapped original image and a mapped tag image comprises:

The Step S111: mark a plurality of tag points in the original image displayed on the display panel to acquire the tag image, wherein four tag points are marked respectively at the left upper corner, the left lower corner, the right upper corner and the right lower corner of the original image to form a tag image. It can be understood that the amount of the tag points in the original image is not limited to four.

The Step S112: sample the original image and the tag image to acquire a sampled original image and a sampled tag image, wherein the original image and the tag image displayed on the display panel are sampled through some parameters of deposing a camera aperture, a film speed (ISO), a shutter, a switch image processing function and through the RGB-YCbCr color space to get the luminance value of the display panel, i.e. the luminance values of the sampled original image and the sampled tag image.

The step S113: respectively cut the original sampled image and the tag sampled image by using a plurality of corner points, to acquire a cut original image and a cut tag image, where a method of determining the corner points comprises:

The step S1131: set up a mask matrix of which the number is relative to the number of the tag points. Here, the four mask matrixes are set up.

The step S1132: convolutively calculate the sampled tag image by using the mask matrixes to get a convolutive value.

The step S1133: determine if Euclidean distance between a point with the convolution value larger than a predetermined threshold value and a top point of the sampled tag image is shortest. Here, the predetermined threshold value is k*gray*16, where k is a luminance mapping coefficient based on the luminance difference of the tag image and the tag sampling image, and gray is a luminance value of the sampled tag image.

The step S1134: define the point with the convolution value larger than the predetermined threshold value and having the shortest Euclidean distance to the top point of the sampled tag image as the corner point.

The step S114: respectively rotate the cut original image and the cut tag image to acquire a rotated original image and a rotated tag image. Here, because the camera and the display panel are located on the horizontal surface (or vertical surface). If not, a space will appear the right upper corner and right left corner of the cut original image and the cut tag image.

The step S115: respectively cut again and stretching the rotated original image and the rotated tag image to acquire a stretched original image and a stretched tag image.

The step S116: respectively black-pixel-insert the stretched original image and the stretched tag image, and fill a black pixel by using a linear interpolation method to acquire the mapped original image and the mapped tag image. Here, the resolution of the mapped original image is same as the resolution of the original image and the resolution of the mapped tag image is same as the resolution of the original image.

In the Step S120, the mapped original image is divided into a plurality of mapped original images and the mapped tag image is divided into a plurality of mapped tag sub-images. Here, in order to avoid the uneven luminance of the display panel (such as LCD panel) resulting from the back light and from the sampling program of the camera, the mapped original image and the mapped tag image is divided.

In the step S130, acquire a normal area and a defective area of the mapped original sub-images.

Here, the step of acquiring the normal area and the defective area of the mapped original sub-images further comprises:

The step S131: acquiring a luminance histogram of the mapped original sub-image.

The step S132: determining the maximum luminance value and the minimum luminance value based on the luminance histogram.

The step S133: determining if a luminance value of a pixel in the mapping original sub-image is larger than the minimum luminance value and smaller than the maximum luminance value, wherein if the determination is yes, i.e. the luminance value of the pixel in the mapping original sub-image is larger than the minimum luminance value and smaller than the maximum luminance value, the pixel of the mapped original sub-image is the normal area; if the determination is no, the luminance value of the pixel in the mapping original sub-image is not larger than the minimum luminance value or smaller than the maximum luminance value, the pixel of the mapped original sub-image is the defective area.

Further, in the step S132, a method of determining the maximum luminance value and the minimum luminance value comprises:

The step S1321: in the luminance histogram, a determining amount ratio of the maximum luminance value and the minimum luminance value is not smaller than a predetermining amount ratio of a maximum luminance initial value and a minimum luminance initial value, such as the maximum luminance initial value and the minimum luminance initial value of the pixels which are 80% in front of the amount in the luminance histogram.

The step S1322: compute a first weighted average value larger than the luminance value of the pixel in the mapped original sub-image of the maximum luminance initial value, and compute a second weighted average value smaller than the luminance value of the pixel in the mapped original sub-image of the minimum luminance initial value.

Step S1323: when a different value between the first weighted average value and the maximum luminance initial value is larger than a threshold value, and a different value between the minimum luminance initial value and the second weighted average value is larger than the threshold value, the maximum luminance initial value and the minimum luminance initial value are respectively defined as the maximum luminance value and the minimum luminance value; or when the difference value between the first weighted average value and the maximum luminance initial value is not larger than the threshold value and/or the difference value between the second weighted average value and the minimum luminance initial value is not larger than the threshold value, the predetermined amount ratio pluses 0.01 and the maximum luminance initial value and the minimum luminance initial value are redefined.

Further, in the step S132, a method of determining the maximum luminance value and the minimum luminance value based on the luminance histogram comprises when the predetermined amount ratio is 100%, the maximum luminance initial value and the minimum luminance initial value are defined as the maximum luminance value and the minimum luminance value.

In the step S140, merge the mapped original sub-images to discriminate the normal area and the defective area of the mapped original sub-images;

In the step S150, correct the discriminated normal area and the discriminated defective area of the mapped original sub-images by using the mapped tag image and the tag image to acquire a defect location of the display panel.

Here, the method of correcting the discriminated normal area and the discriminated defective area of the mapped original sub-images comprises:

The step S151: computing a plurality of tag points in the stretched tag image and a plurality of corresponding coordinate deviation values of the tag points of the tag image;

The step S152: correcting the distinguished normal area and the distinguished defective area of the mapped original image by using the corresponding coordinate deviation values.

In summary, according to the automatic detection method for defects of a display panel of the embodiments of the present invention, the location of the defect and the difference between the defective area and the normal area can be accurately acquired to quantify and discriminate the defects of the display panel.

The above-described embodiments of the invention only, and not to limit the patent scope of the present invention, therefore, the use of all contents of the specification and drawings of the present invention is made equivalent structures or equivalent conversion process, either directly or indirectly in the other the relevant art, are included within the same reason the patent scope of the present invention.

What is claimed is:

1. An automatic detection method for defects of a display panel, comprising:
   acquiring a tag image, a mapped original image and a mapped tag image;
   dividing the mapped original image into a plurality of mapped original sub-images, and dividing the mapped tag image into a plurality of mapped tag sub-images;
   acquiring a normal area and a defective area of the mapped original sub-images;
   merging the mapped original sub-images to discriminate the normal area and the defective area of the mapped original sub-images;
   correcting the discriminated normal area and the discriminated defective area of the mapped original sub-images by using the mapped tag image and the tag image to acquire a defect location of the display panel;
   wherein the step of acquiring a tag image, a mapping original image and a mapping tag image further comprises:
   marking a plurality of tag points in the original image displayed on the display panel to acquire the tag image;
   sampling the original image and the tag image to acquire a sampled original image and a sampled tag image;
   respectively cutting the original sampled image and the tag sampled image by using a plurality of corner points, to acquire a cut original image and a cut tag image;
   respectively rotating the cut original image and the cut tag image to acquire a rotated original image and a rotated tag image;
   respectively cutting again and stretching the rotated original image and the rotated tag image to acquire a stretched original image and a stretched tag image;
   respectively black-pixel-inserting the stretched original image and the stretched tag image, and filling a black pixel by using a linear interpolation method to acquire the mapped original image and the mapped tag image.

2. The automatic detection method as claimed in claim 1, wherein resolution of the mapped original image is same as resolution of the original image, and resolution of the mapped tag image is same as resolution of the original image.

3. The automatic detection method as claimed in claim 1, wherein a method of determining the corner points comprises:
   setting up a plurality of mask matrixes, wherein amount of the mask matrixes is same as amount of the tag points;
   convolution calculating the sampled tag image by using the mask matrixes to get a convolution value;
   determining if Euclidean distance between a point with the convolution value larger than a predetermined threshold value and a top point of the sampled tag image is shortest;
   defining the point with the convolution value larger than the predetermined threshold value and having the shortest Euclidean distance to the top point of the sampled tag image as the corner point.

4. The automatic detection method as claimed in claim 2, wherein a method of determining the corner points comprises:
  setting up a plurality of mask matrixes, wherein amount of the mask matrixes is same as amount of the tag points;
  convolution calculating the tag image by using the mask matrixes to get a convolution value;
  determining if Euclidean distance between a point with the convolution value larger than a predetermined threshold value and a top point of the sampled tag image is shortest;
  defining the point with the convolution value larger than the predetermined threshold value and having the shortest Euclidean distance to the top point of the sampled tag image as the corner point.

5. The automatic detection method as claimed in claim 1, wherein the step of acquiring the normal area and the defective area of the mapped original sub-image further comprises:
  acquiring a luminance histogram of the mapped original sub-image;
  determining the maximum luminance value and the minimum luminance value based on the luminance histogram;
  determining if a luminance value of a pixel in the mapping original sub-image is larger than the minimum luminance value and smaller than the maximum luminance value;
  if the luminance value of the pixel in the mapping original sub-image is larger than the minimum luminance value and smaller than the maximum luminance value, the pixel of the mapped original sub-image is the normal area.

6. The automatic detection method as claimed in claim 5, wherein if the luminance value of the pixel in the mapped original sub-image is not larger than the minimum luminance value or smaller than the maximum luminance value, the pixel of the mapped original sub-image is the defective area.

7. The automatic detection method as claimed in claim 5, wherein a method of determining the maximum luminance value and the minimum luminance value comprises:
  in the luminance histogram, a determining amount ratio of the maximum luminance value and the minimum luminance value is not smaller than a predetermining amount ratio of a maximum luminance initial value and a minimum luminance initial value;
  computing a first weighted average value larger than the luminance value of the pixel in the mapped original sub-image of the maximum luminance initial value, and computing a second weighted average value smaller than the luminance value of the pixel in the mapped original sub-image of the minimum luminance initial value;
  when a different value between the first weighted average value and the maximum luminance initial value is larger than a threshold value, and a different value between the minimum luminance initial value and the second weighted average value is larger than the threshold value, the maximum luminance initial value and the minimum luminance initial value are respectively defined as the maximum luminance value and the minimum luminance value.

8. The automatic detection method as claimed in claim 6, wherein a method of determining the maximum luminance value and the minimum luminance value comprises:
  in the luminance histogram, a determining amount ratio of the maximum luminance value and the minimum luminance value is not smaller than a predetermining amount ratio of a maximum luminance initial value and a minimum luminance initial value;
  computing a first weighted average value larger than the luminance value of the pixel in the mapped original sub-image of the maximum luminance initial value, and computing a second weighted average value smaller than the luminance value of the pixel in the mapped original sub-image of the minimum luminance initial value;
  when a different value between the first weighted average value and the maximum luminance initial value is larger than a threshold value, and a different value between the minimum luminance initial value and the second weighted average value is larger than the threshold value, the maximum luminance initial value and the minimum luminance initial value are respectively defined as the maximum luminance value and the minimum luminance value.

9. The automatic detection method as claimed in claim 7, wherein when the difference value between the first weighted average value and the maximum luminance initial value is not larger than the threshold value and/or the difference value between the second weighted average value and the minimum luminance initial value is not larger than the threshold value, the predetermined amount ratio pluses 0.01 and the maximum luminance initial value and the minimum luminance initial value are redefined.

10. The automatic detection method as claimed in claim 8, wherein when the difference value between the first weighted average value and the maximum luminance initial value is not larger than the threshold value and/or the difference value between the second weighted average value and the minimum luminance initial value, the predetermined amount ratio pluses 0.01 and the maximum luminance initial value and the minimum luminance initial value are redefined.

11. The automatic detection method as claimed in claim 7, wherein a method of determining the maximum luminance value and the minimum luminance value comprises:
  when the predetermined amount ratio is 1, the maximum luminance initial value and the minimum luminance initial value are defined as the maximum luminance value and the minimum luminance value.

12. The automatic detection method as claimed in claim 8, wherein a method of determining the maximum luminance value and the minimum luminance value comprises:
  when the predetermined amount ratio is 1, the maximum luminance initial value and the minimum luminance initial value are defined as the maximum luminance value and the minimum luminance value.

13. The automatic detection method as claimed in claim 1, wherein the step of correcting the distinguished normal area and the distinguished defective area of the mapped original sub-images comprises:
  computing a plurality of tag points in the stretched tag image and a plurality of corresponding coordinate deviation values of the tag points of the tag image;
  correcting the distinguished normal area and the distinguished defective area of the mapped original image by using the corresponding coordinate deviation values.

* * * * *